United States Patent [19]

Déziel et al.

[11] Patent Number: 5,830,864
[45] Date of Patent: *Nov. 3, 1998

[54] ANTIHERPES PEPTIDE DERIVATIVES HAVING A UREIDO N-TERMINUS

[75] Inventors: Robert Déziel, Ville Mont-Royal; Neil Moss; Raymond Plante, both of Laval, all of Canada

[73] Assignee: Boehringer Ingelheim (Canada), Ltd., Quebec, Canada

[ * ] Notice: The term of this patent shall not extend beyond the expiration date of Pat. No. 5,574,015.

[21] Appl. No.: 502,981

[22] Filed: Jul. 17, 1995

Related U.S. Application Data

[63] Continuation of Ser. No. 25,682, Mar. 3, 1993, abandoned, which is a continuation-in-part of Ser. No. 849,922, Mar. 12, 1992, abandoned.

[51] Int. Cl.⁶ ............................. A61K 38/07; C07K 5/10
[52] U.S. Cl. ............................. 514/18; 514/17; 530/330; 530/331
[58] Field of Search ........................ 514/18, 17; 530/330, 530/331

[56] References Cited

U.S. PATENT DOCUMENTS 5,476,841 12/1995 Deziel et al. ............................. 514/17
5,574,015 11/1996 Beaulieu et al. ........................... 514/18

FOREIGN PATENT DOCUMENTS 411334  2/1991  European Pat. Off. .
461546  12/1991  European Pat. Off. .

*Primary Examiner*—Cecilia J. Tsang
*Assistant Examiner*—Anish Gupta
*Attorney, Agent, or Firm*—R. P. Raymond; M-E. M. Devlin; A. R. Stempel

[57] ABSTRACT

Disclosed herein are peptide derivatives of the formula

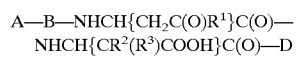

wherein A is a terminal group, for example, an alkylaminocarbonyl or a phenylalkylaminocarbonyl; B is an amino acid residue; $R^1$ is alkyl, cycloalkyl or a disubsubstituted amino; $R^2$ is hydrogen or alkyl and $R^3$ is alkyl, or $R^2$ is hydrogen and $R^3$ is phenylakyl, or $R^2$ and $R^3$ are joined to form a cycloalkyl; and D is a terminal unit, for example, an alkylamino or a monovalent amino acid radical such as NHCH(alkyl)C(O)OH. The derivatives are useful in treating herpes infections.

7 Claims, No Drawings

SEQUENCE LISTING ( 1 ) GENERAL INFORMATION:

( i i i ) NUMBER OF SEQUENCES: 38

( 2 ) INFORMATION FOR SEQ ID NO:1:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear ( i i ) MOLECULE TYPE: peptide ( i x ) FEATURE:

( x i ) SEQUENCE DESCRIPTION: SEQ ID NO:1:

Xaa  Xaa  Xaa  Xaa  Xaa
 1                         5

( 2 ) INFORMATION FOR SEQ ID NO:2:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:2:

Xaa  Xaa  Xaa  Xaa  Xaa

Xaa Xaa Xaa Xaa Xaa
1               5

(2) INFORMATION FOR SEQ ID NO:3:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:3:

Xaa Xaa Xaa Xaa Xaa
1               5

(2) INFORMATION FOR SEQ ID NO:4:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:4:

Xaa Xaa Xaa Xaa Xaa
1               5

(2) INFORMATION FOR SEQ ID NO:5:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:5:

Xaa Xaa Xaa Xaa Xaa
1               5

(2) INFORMATION FOR SEQ ID NO:6:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:6:

Xaa Xaa Xaa Xaa Xaa
1               5

(2) INFORMATION FOR SEQ ID NO:7:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:7:

Xaa Xaa Xaa Xaa Xaa ( 2 ) INFORMATION FOR SEQ ID NO:8:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:8:

Xaa Xaa Xaa Xaa Xaa
1                 5

( 2 ) INFORMATION FOR SEQ ID NO:9:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:9:

Xaa Xaa Xaa Xaa Xaa
1                 5

( 2 ) INFORMATION FOR SEQ ID NO:10:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:10:

Xaa Xaa Xaa Xaa Xaa
1                 5

( 2 ) INFORMATION FOR SEQ ID NO:11:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:11:

Xaa Xaa Xaa Xaa Xaa
1                 5

( 2 ) INFORMATION FOR SEQ ID NO:12:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:12:

Xaa Xaa Xaa Xaa Xaa ( 2 ) INFORMATION FOR SEQ ID NO:13:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:13:

Xaa Xaa Xaa Xaa Xaa
1                  5

( 2 ) INFORMATION FOR SEQ ID NO:14:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:14:

Xaa Xaa Xaa Xaa Xaa
1                  5

( 2 ) INFORMATION FOR SEQ ID NO:15:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:15:

Xaa Xaa Xaa Xaa Xaa
1                  5

( 2 ) INFORMATION FOR SEQ ID NO:16:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:16:

Xaa Xaa Xaa Xaa Xaa
1                  5

( 2 ) INFORMATION FOR SEQ ID NO:17:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:17:

Xaa Xaa Xaa Xaa Xaa ( 2 ) INFORMATION FOR SEQ ID NO:18:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:18:

Xaa Xaa Xaa Xaa Xaa
1                   5

( 2 ) INFORMATION FOR SEQ ID NO:19:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:19:

Xaa Xaa Xaa Xaa Xaa
1                   5

( 2 ) INFORMATION FOR SEQ ID NO:20:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:20:

Xaa Xaa Xaa Xaa Xaa
1                   5

( 2 ) INFORMATION FOR SEQ ID NO:21:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:21:

Xaa Xaa Xaa Xaa Xaa
1                   5

( 2 ) INFORMATION FOR SEQ ID NO:22:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:22:

Xaa Xaa Xaa Xaa Xaa

```
1               5
```

(2) INFORMATION FOR SEQ ID NO:23:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:23:

```
Xaa   Xaa   Xaa   Xaa   Xaa
1                       5
```

(2) INFORMATION FOR SEQ ID NO:24:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:24:

```
Xaa   Xaa   Xaa   Xaa   Xaa
1                       5
```

(2) INFORMATION FOR SEQ ID NO:25:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:25:

```
Xaa   Xaa   Xaa   Xaa   Xaa
1                       5
```

(2) INFORMATION FOR SEQ ID NO:26:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:26:

```
Xaa   Xaa   Xaa   Xaa   Xaa
1                       5
```

(2) INFORMATION FOR SEQ ID NO:27:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:27:

```
Xaa   Xaa   Xaa   Xaa   Xaa
```

(2) INFORMATION FOR SEQ ID NO:28:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:28:

Xaa Xaa Xaa Xaa Xaa
1                 5

(2) INFORMATION FOR SEQ ID NO:29:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:29:

Xaa Xaa Xaa Xaa Xaa
1                 5

(2) INFORMATION FOR SEQ ID NO:30:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:30:

Xaa Xaa Xaa Xaa Xaa
1                 5

(2) INFORMATION FOR SEQ ID NO:31:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:31:

Xaa Xaa Xaa Xaa Xaa
1                 5

(2) INFORMATION FOR SEQ ID NO:32:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:32:

Xaa Xaa Xaa Xaa Xaa 1               5

( 2 ) INFORMATION FOR SEQ ID NO:33:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:33:

Xaa   Xaa   Xaa   Xaa   Xaa
1                           5

( 2 ) INFORMATION FOR SEQ ID NO:34:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:34:

Xaa   Xaa   Xaa   Xaa   Xaa
1                           5

( 2 ) INFORMATION FOR SEQ ID NO:35:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:35:

Xaa   Xaa   Xaa   Xaa   Xaa
1                           5

( 2 ) INFORMATION FOR SEQ ID NO:36:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:36:

Xaa   Xaa   Xaa   Xaa   Xaa
1                           5

( 2 ) INFORMATION FOR SEQ ID NO:37:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:37:

Xaa   Xaa   Xaa   Xaa   Xaa (2) INFORMATION FOR SEQ ID NO:38:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:38:

ANTIHERPES PEPTIDE DERIVATIVES HAVING A UREIDO N-TERMINUS

This is a continuation of application Ser. No. 08/025,682, filed Mar. 3, 1993, now abandoned, which is a continuation-in-part of application Ser. No. 07/849,922, filed Mar. 12, 1992, now abandoned.

FIELD OF INVENTION

This invention relates to peptide derivatives having antiviral properties and to means for using the derivatives to treat viral infections. More specifically, the invention relates to peptide derivatives (hereinafter called "peptides") exhibiting activity against herpes viruses, to pharmaceutical compositions comprising the peptides, and to methods of using the peptides to inhibit the replication of herpes virus and to treat herpes infections.

BACKGROUND OF THE INVENTION

Herpes viruses inflict a wide range of diseases against humans and animals. For instance, herpes simplex viruses, types 1 and 2 (HSV-1 and HSV-2), are responsible for cold sores and genital lesions, respectively; varicella zoster virus (VZV) causes chicken pox and shingles; and the Epstein-Barr virus (EBV) causes infectious mononucleosis.

Over the past two decades, a class of compounds known as the purine and pyrimidine nucleoside analogs has received the most attention by investigators in the search for new therapeutic agents for treatment of herpes virus infections. As a result, several nucleoside analogs have been developed as antiviral agents. The most successful to date is acyclovir which is the agent of choice for treating genital herpes simplex infections.

Nevertheless, in spite of some significant advances, the need for effective, safe therapeutic agents for treating herpes viral infections continues to exist. For a review of current therapeutic agents in this area, see M. C. Nahata, "Antiviral Drugs: Pharmacokinetics, Adverse Effects and Therapeutic Use", J. Pharm. Technol., 3, 100 (1987).

The present application discloses a group of peptide derivatives having activity against herpes viruses. The relatively selective action of these peptides against herpes viruses, combined with a wide margin of safety, renders the peptides as desirable agents for combating herpes infections.

The following references disclose peptides or peptide derivatives which have been associated with antiherpes activity:

B. M. Dutia et al., Nature, 321, 439 (1986),
E. A. Cohen et al., Nature, 321, 441 (1986),
J. H. Subak-Sharpe et al., UK patent application 2185024, published Jul. 8, 1987,
P. Gaudreau et al., J. Biol. Chem., 262, 12413 (1987),
E. A. Cohen et al., U.S. Pat. No. 4,795,740, Jan. 3, 1989,
R. Freidinger et al., U.S. Pat. No. 4,814,432, Mar. 21, 1989,
V. M. Garskey et al., U.S. Pat. No. 4,837,304, Jun. 6, 1989,
R. Colonno et al., U.S. Pat. No. 4,845,195, Jul. 4, 1989,
P. Gaudreau et al., J. Med. Chem., 33, 723 (1990),
J. Adams et al., European patent application 408,973, published Jan. 23, 1991,
P. L. Beaulieu et al., European patent application 411,332, published Feb. 6, 1991,
J. Adams et al., European patent application 411,333, published Feb. 6, 1991,
J. Adams et al., European patent application 411,334, published Feb. 6, 1991,
R. L. Tolman et al., European patent application 412, 595, published Feb. 13, 1991,
W. T. Ashton et al., European patent application 438,873, published Jul. 31, 1991,
P. L. Beaulieu et al., European patent application 461,546, published Dec. 18, 1991, and
P. Gaudreau et al., J. Med. Chem., 35, 346 (1992).

The subject peptides of the previous reports can be distinguished from the peptides of the present application by characteristic structural and biological differences.

Abbreviations and symbols used hereinafter are defined in the "Details of the Invention" section of this application.

SUMMARY OF THE INVENTION

The peptides of this invention are represented by formula 1

$$A-B-NHCH\{CH_2C(O)R^1\}C(O)-NHCH\{CR^2(R^3)COOH\}C(O)-D \qquad 1$$

wherein
A is $R^4NHC(O)$ wherein $R^4$ is
  (i) (2–10C)alkyl,
  (ii) an unsaturated alkyl selected from the group consisting of 1-(2-propenyl)-3-butenyl, 1-methyl-1-(2-propenyl)-3-butenyl and 1-ethyl-1-(2-propenyl)-3-butenyl,
  (iii) phenyl(lower)alkyl or phenyl(lower)alkyl monosubstituted with lower alkyl, halo, hydroxy, lower alkyl or lower alkoxy, or
  (iv) 1-(lower alkyl)-(lower cycloalkyl);
B is an amino acid residue or derived amino acid residue of the formula $NHCHR^5C(O)$ wherein $R^5$ is 1-tricyclo$\{3.3.1.1^{3,7}\}$decyl, lower alkyl or lower alkyl monosubstituted with carboxy, hydroxy, mercapto or benzyloxy;
$R^1$ is lower alkyl, lower cycloalkyl, 1-(lower alkyl)-(lower alkyl) or $NR^6R^7$ wherein $R^6$ is hydrogen or lower alkyl and $R^7$ is lower alkyl, or $R^6$ and $R^7$, together with the nitrogen atom to which they are attached form a pyrrolidino, piperidino, piperazino or N-methylpiperazino;
$R^2$ is hydrogen or lower alkyl and $R^3$ is lower alkyl, or $R^2$ is hydrogen and $R^3$ is phenyl-(1–4C)alkyl, or $R^2$ and $R^3$ together with the carbon atom to which they are attached form a lower cycloalkyl; and
D is $NHR^8$ wherein $R^8$ is (4–9C)alkyl, or D is NHCH $(R^9)$—Z wherein $R^9$ is (4–9C)alkyl, lower cycloalkyl or (lower cycloalkyl)-(lower alkyl) and Z is $CH_2OH$, $C(O)OH$, $C(O)NH_2$ or $C(O)OR^{10}$ wherein $R^{10}$ is lower alkyl;
or a therapeutically acceptable salt thereof.

A preferred group of the peptides of this invention is represented by formula 1 wherein A is (2–10C) alkylaminocarbonyl, 1-(2-propenyl)-3-butenylaminocarbonyl, 1-methyl-1-(2-propenyl)-3-butenylaminocarbonyl, 1-ethyl-1-(2-propenyl)-3-butenylaminocarbony, benzylaminocarbonyl, (1-propylcyclopentyl)aminocarbonyl, (1-ethylcyclohexyl)aminocarbonyl or (1-propylcyclohexyl)aminocarbonyl;
B is $NHCHR^5C(O)$ wherein $R^5$ is 1-tricyclo$\{3.3.1.1^{3,7}\}$decyl, lower alkyl or lower alkyl mono-substituted with carboxy, hydroxy or mercapto; and
$R^1$, $R^2$, $R^3$ and D are as defined hereinabove; or a therapeutically acceptable salt thereof.

A more preferred group of the peptides is represented by formula 1 wherein A is propylaminocarbonyl, (1-methylethyl)aminocarbonyl, (1,1-dimethylethyl)

aminocarbonyl, (1-methylpropyl)aminocarbonyl, (1-ethylpropyl)aminocarbonyl, (1,1-dimethylbutyl) aminocarbonyl, (1,1,3,3-tetramethylbutyl)aminocarbonyl, (1-ethylbutyl)aminocarbonyl, (1-propylbutyl) aminocarbonyl, (1-ethylpentyl)aminocarbonyl, (2-propylpentyl)aminocarbonyl, 1-methyl-1-propylbutylaminocarbonyl, 1-ethyl-1-propylbutyl-aminocarbonyl, 1,1-dipropylbutylaminocarbonyl, (1-propylcyclopentyl)aminocarbonyl, (1-ethylcyclohexyl) aminocarbonyl, (1-propylcyclohexyl)aminocarbonyl, 1-(2-propenyl)-3-butenylaminocarbonyl, 1-methyl-1-(2-propenyl)-3-butenylaminocarbonyl or 1-ethyl-1-(2-propenyl)-3-butenylaminocarbonyl; B is an amino acid residue of (S)-α-aminotricyclo{3.3.1.1$^{3,7}$}decane-1-acetic acid, (S)-2-amino-3-hydroxy-3-methyl-butanoic acid or (R)-2-amino-3-mercapto-3-methylbutanoic acid, or an amino acid residue selected from Tbg, Val, Asp{(R)—Me} and Asp(diMe); $R^1$ is lower alkyl, lower cycloalkyl, N,N-dimethylamino, N,N-diethylamino, pyrrolidino or piperidino; $R^2$ is hydrogen and $R^3$ is methyl, ethyl, 1-methylethyl, 1,1-dimethylethyl or benzyl, and the carbon atom bearing $R^2$ and $R^3$ has the (R)-configuration, or $R^2$ and $R^3$ each independently is methyl or ethyl, or $R^2$ and $R^3$ together with the carbon atom to which they are attached form a cyclobutyl, cyclopentyl or cyclohexyl; and D is $NHR^8$ wherein $R^8$ is 2-methylpropyl, 2,2-dimethylpropyl, 1(R),2,2-trimethylpropyl, 1,1,2,2-tetramethylpropyl, 1(R)-ethyl-2,2-dimethylpropyl, 2-(R,S)-methylbutyl, 2,2-dimethylbutyl, 3,3-dimethylbutyl, 1(R),2,2-trimethylbutyl, 1(R),3,3-trimethylbutyl, 2-ethylbutyl, 2,2-diethylbutyl, 2-ethyl-1-(R)-methylbutyl, 2-ethyl-2-methylbutyl and 2,2-dimethylpentyl, or D is $NHCH(R^9)$—Z wherein the carbon atom bearing $R^9$ has the (S)-configuration, $R^9$ is 1-methylpropyl, 2-methylpropyl, 2,2-dimethylpropyl or cyclohexylmethyl and Z is $CH_2OH$, C(O)OH, C(O)NH$_2$ or C(O)OR$^{10}$ wherein $R^{10}$ is methyl, ethyl or propyl; or a therapeutically acceptable salt thereof.

A most preferred group of the peptides is represented by formula 1 wherein A is (1-methylethyl)aminocarbonyl, (1,1-dimethylethyl)aminocarbonyl, (1-ethylpropyl)aminocarbonyl, (1-propylbutyl)aminocarbonyl, 1-methyl-1-propylbutylaminocarbonyl, 1-ethyl-1-propylbutylaminocarbonyl, 1,1-dipropylbutylaminocarbonyl or (1-propylcyclopentyl) aminocarbonyl; B, $R^1$, $R^2$ and $R^3$ are as defined in the last instance; and D is NHR$^8$ wherein $R^8$ is 2,2-dimethylpropyl, 1(R),2,2-trimethylpropyl, 1(R)-ethyl-2,2-dimethyl-propyl, 2,2-dimethylbutyl or 3,3-dimethylbutyl, or D is NHCH(R$^9$) —Z wherein the carbon atom bearing $R^9$ has the (S)-configuration, $R^9$ is 2,2-dimethylpropyl and Z is $CH_2OH$, C(O)OH, C(O)NH$_2$ or C(O)OR$^{10}$ wherein $R^{10}$ is methyl, ethyl or propyl; or a therapeutically acceptable salt thereof.

Included within the scope of this invention is a pharmaceutical composition comprising an anti-herpes virally effective amount of a peptide of formula 1, or a therapeutically acceptable salt thereof, and a pharmaceutically or veterinarily acceptable carrier.

Also included within the scope of this invention is a cosmetic composition comprising a peptide of formula 1, or a therapeutically acceptable salt thereof, and a physiologically acceptable carrier suitable for topical application.

An important aspect of the invention involves a method of treating a herpes viral infection in a mammal by administering to the mammal an anti-herpes virally effective amount of the peptide of formula 1, or a therapeutically acceptable salt thereof.

Another important aspect involves a method of inhibiting the replication of herpes virus by contacting the virus with a herpes viral ribonucleotide reductase inhibiting amount of the peptide of formula 1, or a therapeutically acceptable salt thereof.

Still another aspect involves a method of treating a herpes viral infection in a mammal by administering thereto an antiherpes virally effective amount of a combination of the peptide of formula 1, or a therapeutically acceptable salt thereof, and an antiviral nucleoside analog. A pharmaceutical composition comprising the combination is also within the scope of this invention.

Processes for preparing the peptides of formula 1 are described hereinafter.

Details of the Invention
GENERAL

Alternatively, formula 1 can be illustrated as:

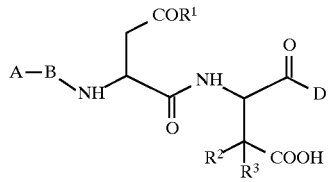

The term "residue" with reference to an amino acid or amino acid derivative means a radical derived from the corresponding α-amino acid by eliminating the hydroxyl of the carboxy group and one hydrogen of the α-amino group.

In general, the abbreviations used herein for designating the amino acids and the protective groups are based on recommendations of the IUPAC-IUB Commision of Biochemical Nomenclature, see European Journal of Biochemistry 138, 9 (1984). For instance, Val, Ile, Asp, and Leu represent the residues of L-valine, L-isoleucine, L-aspartic acid and L-leucine, respectively.

The asymmetric carbon atoms residing in the principal linear axis (i.e. the backbone) of the peptides of formula 1, exclusive of the terminal group A and Z (of D) but including the carbon atom bearing the "$R^9$" when D is NHCH(R$^9$)—Z as defined herein, have an S configuration. An exception occurs, however, when B is an amino acid residue having a 2-mercaptoalkyl side chain whereby the carbon atom in the linear axis bearing that side chain preferably has the R configuration. Asymmetric carbon atoms residing in the side chain of an amino acid or derived amino acid residue, in the terminal group A, in the terminal group D when D represents NHR$^8$ as defined herein, may have the S or R configuration.

The symbol "Tbg" represents the amino acid residue of (S)-2-amino-3,3-dimethylbutanoic acid. The symbol "γMeLeu" represents the amino acid residue of (S)-2-amino-4,4-dimethylpentanoic acid. The symbol "γMeLeucinol" represents (S)-2-amino-4,4-dimethylpentanol with one hydrogen removed from the α-amino group.

The symbols "Me", "Et", "Pr" and "Bu" represent the alkyl radicals methyl, ethyl, propyl and butyl, respectively.

The symbols "MePr$_2$C" and "PrMe$_2$C", for example, represent the radicals 1-methyl-1-propylbutyl and 1,1-dimethylbutyl, respectively.

Other symbols used herein are: Asp(cyBu) for the residue of (S)-α-amino-1-carboxycyclobutaneacetic acid; Asp (cyPn) for the residue of (S)-α-amino-1-carboxycyclopentaneacetic acid. The symbol "Asp(diMe)" represents the residue of 2(S)-amino-3,3-dimethylbutanedioic acid, i.e. 3,3-dimethyl-L-aspartic acid. Similarly, Asp(diEt), Asp{(R)—Me} and Asp{(R)-iPr} represent the residues of 3,3-diethyl-L-aspartic acid, 3(R)-methyl-L-aspartic acid (i.e. {S—(R*, S*)}-2-amino-3-methylbutanedioic acid and 3(R)-(1-methylethyl)-L-aspartic acid, respectively.

The term "halo" as used herein means a halo radical selected from bromo, chloro, fluoro or iodo.

The term "adamantyl" is used herein to designate the "1-tricyclo{3.3.1.1$^{3,7}$}decanyl" radical.

The term "(2–10C)alkyl" as used herein, either alone or in combination with another radical, means straight and branched chain alkyl radicals containing from two to ten carbon atoms and includes ethyl, butyl, 1-methylpropyl, 1-ethylpropyl, 1-propylbutyl, 2-propylpentyl and the like.

The term "(4–9C)alkyl" as used herein means straight and branched chain alkyl radicals containing from four to nine carbon atoms and includes, for example, 1-methylpropyl, 2-methylpropyl, 1,2,2-trimethylproply, 3,3-dimethylbutyl, 1-ethyl-2,2-dimethylbutyl and 4,4-dimethylpentyl.

The term "lower alkyl" as used herein, either alone or in combination with another radical, means straight chain alkyl radicals containing one to six carbon atoms and branched chain alkyl radicals containing three to six carbon atoms and includes methyl, ethyl, propyl, butyl, hexyl, 1-methylethyl, 1-methylpropyl, 2-methylpropyl and 1,1-dimethylethyl.

The term "1-(lower alkyl)-(lower cycloalkyl)" as used herein means a lower cycloalkyl radical bearing a lower alkyl substituent at position 1; for example, 1-ethylcyclopropyl, 1-ethylcyclohexyl, 1-propylcyclopentyl and 1-propylcyclohexyl.

The term "lower cycloalkyl" as used herein, either alone or in combination with another radical, means saturated cyclic hydrocarbon radicals containing from three to six carbon atoms and includes cyclopropyl, cyclobutyl, cyclopentyl and cyclohexyl.

The term "lower alkoxy" as used herein means straight chain alkoxy radicals containing one to four carbon atoms and branched chain alkoxy radicals containing three to four carbon atoms and includes methoxy, ethoxy, propoxy, 1-methylethoxy, butoxy and 1,1-dimethylethoxy. The latter radical is known commonly as tert-butoxy.

The term "phenyl-(1–4C)alkyl" as used herein means phenylalkyl radicals wherein the alkyl portion thereof is straight or branched chain alkyl containing from one to four carbon atoms and includes benzyl, 2-phenylethyl, 3-phenylpropyl, 2-methyl-2-phenylethyl {PhCH(CH$_3$)CH$_2$}, 1-ethyl-2-phenylethyl {PhCH$_2$CH(C$_2$H$_5$)} and the like.

The term "phenyl(lower)alkanoyl" as used herein, either alone or in combination with another radical, means phenyl substituted 1-oxoalkyl radicals wherein the 1-oxoalkyl portion thereof is a straight or branched chain 1-oxoalkyl containing from two to six carbon atoms; for example, 1-oxo-3-phenylpropyl and 1-oxo-5-methyl-6-phenylhexyl.

The term "pharmaceutically acceptable carrier" or "veterinarily acceptable carrier" as use herein means a non-toxic, generally inert vehicle for the active ingredient which does not adversely affect the ingredient.

The term "physiologically acceptable carrier" as used herein means an acceptable cosmetic vehicle of one or more non-toxic excipients which do not react with or reduce the effectiveness of the active ingredient contained therein.

The term "veterinarily acceptable carrier" as used herein means a physiologically acceptable vehicle for administering drug substances to domestic animals comprising one or more non-toxic pharmaceutically acceptable excipients which do not react with the drug substance or reduce its effectiveness.

The term "effective amount" means a predetermined antiviral amount of the antiviral agent, i.e. an amount of the agent sufficient to be effective against the viral organisms in vivo.

The term "coupling agent" as used herein means an agent capable of effecting the dehydrative coupling of an amino acid or peptide free carboxy group with a free amino group of another amino acid or peptide to form an amide bond between the reactants. Similarly, such agents can effect the coupling of an acid and an alcohol to form corresponding esters. The agents promote or facilitate the dehydrative coupling by activating the carboxy group. Descriptions of such coupling agents and activated groups are included in general text books of peptide chemistry; for instance, E. Schröder and K. L. Lübke, "The Peptides", Vol. 1, Academic Press, New York, N.Y., 1965, pp 2–128, and K. D. Kopple, "Peptides and Amino acids", W. A. Benjamin, Inc., New York, N.Y., 1966, pp 33–51. Examples of coupling agents are diphenylphosphoryl azide, 1,1'-carbonyldiimidazole, dicyclohexylcarbodiimide, N-hydroxysuccinimide, or 1-hydroxybenzotriazole in the presence of dicyclohexylcarbodiimide. A very practical and useful coupling agent is (benzotriazol-1-yloxy)tris-(dimethylamino)-phosphonium hexafluorophosphate, described by B. Castro et al., Tetrahedron Letters, 1219 (1975), see also D. Hudson, J. Org. Chem., 53, 617 (1988), either by itself or in the presence of 1-hydroxybenzotriazole. Still another very practical and useful coupling agent is the commercially available 2-(1H-benzotriazol-1-yl)-N,N,N', N'-tetramethyluronium tetrafluoroborate.

Process

The peptides of formula 1 can be prepared by processes which incorporate therein methods commonly used in peptide synthesis such as the classical solution coupling of amino acid residues and/or peptide fragments. Such methods are described, for example, by E. Schröder and K. Lübke, cited above, in the textbook series, "The Peptides: Analysis, Synthesis, Biology", E. Gross et al., Eds., Academic Press, New York, N.Y., 1979–1987, Volumes 1 to 8, and by J. M. Stewart and J. D. Young in "Solid Phase Peptide Synthesis", 2nd ed., Pierce Chem. Co., Rockford, Ill., USA, 1984.

A common feature of the aforementioned processes for the peptides is the protection of the reactive side chain groups of the various amino acid residues or derived amino acid residues (or, if required, non-peptidic fragments of the peptide) with suitable protective groups which will prevent a chemical reaction from occurring at that site until the protective group is ultimately removed. Also common is the protection of an α-amino group on an amino acid or a fragment while that entity reacts at the carboxy group, followed by the selective removal of the α-amino protective group to allow subsequent reaction to take place at that location. Another common feature is the initial protection of the C-terminal carboxyl of the amino acid residue or peptide fragment, if present, which is to become the C-terminal function of the peptide, with a suitable protective group which will prevent a chemical reaction from occurring at that site until the protective group is removed after the desired sequence of the peptide has been assembled.

In general, therefore, a peptide of formula 1 can be prepared by the stepwise coupling, in the order of the sequence of the peptide, of the appropriate amino acid or derived amino acid residues, and non-peptidic fragments of the peptide (such as the N-terminal ureido residue A of peptide), which if required are suitably protected, and eliminating all protecting groups, if present, at the completion of the stepwise coupling to obtain the peptide of formula 1.

A convenient coupling method for incorporating the N-terminal ureido residue "A" of formula 1 is based on a classical method of preparing a urea {see for example, P. A. S. Smith, Org. Reactions, III, 376–377 (1946)} whereby the corresponding isocyanate of the residue to be incorporated is reacted with the terminal α-amino group of an appropriate protected fragment (e.g. protected fragment of H—B—OH or H—B—NHCH{CH$_2$C(O)R$^1$}C(O)—D wherein B, R$^1$ and D are as defined herein) during the stepwise assembly process. In turn, the requisite isocyanates are either commercially available or can be prepared from their readily available corresponding acids according to the method of J. Weinstock, J. Org. Chem., 26, 3511 (1961).

More specific processes are illustrated in the examples hereinafter.

The peptide of formula 1 of this invention can be obtained in the form of a therapeutically acceptable salt. In the instance where a particular peptide has a residue which functions as a base, examples of such salts of the base are those with organic acids, e.g. acetic, lactic, succinic, methanesulfonic or p-toluenesulfonic acid, as well as polymeric acids such as tannic acid or carboxymethyl cellulose, and also salts with inorganic acids such as hydrohalic acids, e.g. hydrochloric acid, or sulfuric acid, or phorphoric acid. If desired, a particular acid addition salt is converted into another acid addition salt, such as a non-toxic, pharmaceutically acceptable salt, by treatment with the appropriate ion exchange resin in the manner described by R. A. Boissonnas et al., Helv. Chim. Acta, 43, 1849 (1960).

In the instance where a particular peptide has one or more free carboxy groups, examples of such salts of the carboxy group are those with the sodium, potassium or calcium cations, or with organic bases, for example, triethylamine or N-methylmorpholine.

Antiherpes Activity

The antiviral activity of the peptides of formula 1 can be demonstrated by biochemical, microbiological and biological procedures showing the inhibitory effect of the compounds on the replication of herpes simplex viruses, types 1 and 2 (HSV-1 and HSV-2), and other herpes viruses, for example, varicella zoster virus (VZV) and Epstein-Barr virus (EBV).

In the examples hereinafter, the inhibitory effect on herpes ribonucleotide reductase is noted for exemplary peptides of formula 1. Noteworthy, in the connection with this specific inhibition of herpes ribonucleotide reductase, is the relatively minimal effect or absence of such an effect of the peptides on cellular ribonucleotide reductase activity required for normal cell replication.

A method for demonstrating the inhibitory effect of the peptides of formula 1 on viral replication is the cell culture technique; see, for example, T. Spector et al., Proc. Natl. Acad. Sci. USA, 82, 4254 (1985).

The therapeutic effect of the peptides can be demonstrated in laboratory animals, for instance, by using an assay based on the murine model of herpes simplex virus-induced ocular disease for antiviral drug testing, described by C. R. Brandt et al., J. Virol. Meth., 36, 209 (1992).

When a peptide of this invention, or one of its therapeutically acceptable salts, is employed as an antiviral agent, it is administered topically or systemically to warm-blooded animals, e.g. humans, pigs or horses, in a vehicle comprising one or more pharmaceutically acceptable carriers, the proportion of which is determined by the solubility and chemical nature of the peptide, chosen route of administration and standard biological practice. For topical administration, the peptide can be formulated in pharmaceutically accepted vehicles containing 0.1 to 5 percent, preferably 0.5 to 2 percent, of the active agent. Such formulations can be in the form of a solution, cream or lotion.

For systemic administration, the peptide of formula 1 is administered by either intravenous, subcutaneous or intramuscular injection, in compositions with pharmaceutically acceptable vehicles or carriers. For administration by injection, it is preferred to use the peptide in solution in a sterile aqueous vehicle which may also contain other solutes such as buffers or preservatives as well as sufficient quantities of pharmaceutically acceptable salts or of glucose to make the solution isotonic.

Suitable vehicles or carriers for the above noted formulations are described in standard pharmaceutical texts, e.g. in "Remington's Pharmaceutical Sciences", 18th ed, Mack Publishing Company, Easton, Penn., 1990.

The dosage of the peptide will vary with the form of administration and the particular active agent chosen. Furthermore, it will vary with the particular host under treatment. Generally, treatment is initiated with small increments until the optimum effect under the circumstances is reached. In general, the peptide is most desirably administered at a concentration level that will generally afford antivirally effective results without causing any harmful or deleterious side effects.

With reference to topical application, the peptide is administered cutaneously in a suitable topical formulation to the infected area of the body e.g. the skin or part of the oral or genital cavity, in an amount sufficient to cover the infected area. The treatment should be repeated, for example, every four to six hours until lesions heal.

With reference to systemic administration, the peptide of formula 1 is administered at a dosage of 10 μg to 500 μg per kilogram of body weight per day, although the aforementioned variations will occur. However, a dosage level that is in the range of from about 10 μg to 200 μg per kilogram of body weight per day is most desirably employed in order to achieve effective results.

Another aspect of this invention comprises a cosmetic composition comprising a herpes viral prophylactic amount of the peptide of formula 1, or a therapeutically acceptable salt thereof, together with a physiologically acceptable cosmetic carrier. Additional components, for example, skin softeners, may be included in the formulation. The cosmetic formulation of this invention is used prophylactically to prevent the outbreak of herpetic lesions of the skin. The formulation can be applied nightly to susceptible areas of the skin. Generally, the cosmetic composition contains less of the peptide than corresponding pharmaceutical compositions for topical application. A preferred range of the amount of the peptide in the cosmetic composition is 0.01 to 0.2 percent by weight.

Although the formulation disclosed hereinabove are indicated to be effective and relatively safe medications for treating herpes viral infections, the possible concurrent administration of these formulations with other antiviral medications or agents to obtain beneficial results is not excluded. Such other antiviral medications or agents include the antiviral nucleosides, for example, acyclovir, and antiviral surface active agents or antiviral interferons such as those disclosed by S. S. Asculai and F. Rapp in U.S. Pat. No. 4,507,281, Mar. 26, 1985.

More specifically with respect to treating herpes viral infections by concurrent administration, it has been found that the antiherpes activity of an antiviral nucleoside analogs can be enhanced synergistically, without the concomitant enhancement of toxic effects, by combining the same with a peptide of formula 1. Accordingly, there is provided herewith a pharmaceutical composition for treating herpes infections in a mammal comprising a pharmaceutically or veterinarily acceptable carrier, and an effective amount of the combination of an antiviral nucleoside analog or a therapeutically acceptable salt thereof, and a ribonucleotide reductase inhibiting peptide of formula 1 or a therapeutically acceptable salt thereof.

Also provided herein is a method of treating herpes viral infections in a mammal. The method comprises administering to the mammal an antiherpes virally effective amount of a combination of a compound of formula 1 or a therapeutically acceptable salt thereof, and an antiviral nucleoside analog or a therapeutically acceptable salt thereof.

The antiviral nucleoside analog employed in the combination is one which is enzymatically convertible (in vivo) to a viral DNA polymerase inhibitor of, and/or an alternative substrate for, a herpes DNA polymerase. The antiviral nucleoside analog can be selected from known nucleoside analogs. Preferred nucleoside analogs of the invention include acyclovir and its analogs; for example, the compounds of formula 2

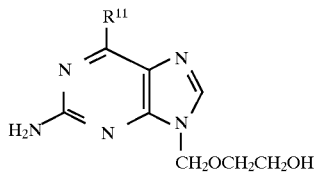

2 wherein $R^{11}$ is hydrogen, hydroxy or amino, or a therapeutically acceptable salt thereof. (Formula 2 wherein $R^{11}$ is hydroxy represents acyclovir.)

Other preferred antiviral nucleoside analogs for use according to the present invention include vidarabine, idoxuridine, trifluridine, ganciclovir, edoxudine, brovavir, fiacitabine, penciclovir, famciclovir and rociclovir.

The term "synergistic effect" when used in relation to the antiviral or antiherpes activity of the above defined combination of the nucleoside analog and peptide of formula 1 means an antiviral or antiherpes effect which is greater than the predictive additive effect of the two individual components of the combination.

When utilizing the combination of this invention for treating herpes infections, the combination is administered to warm blooded animals, e.g. humans, pigs or horses, in a vehicle comprising one or more pharmaceutically acceptable carriers, the proportion of which is determined by the solubility and chemical nature of the nucleoside analog and the peptide of formula 1, chosen route of administration, standard biological practice, and by the relative amounts of the two active ingredients to provide a synergistic antiviral effect. Preferably, the combination is administered topically. For example, the two active agents (i.e. the antiviral nucleoside analog and the peptide of formula 1, or their therapeutically acceptable salts) can be formulated in the form of solutions, emulsions, creams, or lotions in pharmaceutically acceptable vehicles. Such formulation can contain 0.01 to 1.0 percent by weight of the nucleoside analog, or a therapeutically acceptable salt thereof, and about 0.05 to 1 percent by weight of the peptide of formula 1, or a therapeutically acceptable salt thereof.

In any event, the two active agents are present in the pharmaceutical composition in amounts to provide a synergistic antiherpes effect.

The following examples illustrate further this invention. Temperatures are given in degrees Celsius. Solution percentages or ratios express a volume to volume relationship, unless stated otherwise. Nuclear magnetic resonance spectra were recorded on a Bruker 200 MHz spectrometer; the chemical shifts (δ) are reported in parts per million. Abbreviations used in the examples include Boc: tert-butyloxycarbonyl; Bzl: benzyl; Et: ethyl; EtOH: ethanol; EtOAc: ethyl acetate; Et$_2$O: diethyl ether; Me: methyl; MeOH: methanol; Pr: propyl; TLC: thin layer chromatography; THF: tetrahydrofuran.

EXAMPLE 1

Preparation of (1-Ethylpropyl)isocyanate

The title compound was prepared according to a modification of the procedure of J. Weinstock, J. Org. Chem., 26, 3511 (1961): 2-Ethylbutyric acid (10.0 g, 0.086 mol) was suspended in H$_2$O. Sufficient acetone was added to complete solution. The solution was cooled to 0° and a solution of triethylamine (10.2 g, 14 mL, 0.10 mol) in acetone (175 mL) was added. Thereafter, while maintaining the reaction temperature of 0°, a solution of ethyl chloroformate (12.5 g, 0.11 mol) in acetone (45 mL) was added slowly. The mixture was stirred for 30 min at 0° and then a solution of sodium azide (8.6 g, 0.13 mol) in H$_2$O (30 mL) was added dropwise. The mixture was stirred at 0° for 1 h and then poured into an excess of ice water. The aqueous mixture was extracted with toluene (30 mL). The organic phase was dried over MgSO$_4$ and then passed through a filter. The filtrate was kept at 20° until the evolution of N$_2$ ceased. The concentration of 1-ethylpropylisocyanate in the toluene solution was estimated by $^1$H NMR to be 290 mg/mL (8.4 g, 86% yield). The toluene solution of the product was stored under argon at room temperature (20°–22°) until use.

By following the procedure of this example but replacing 2-ethylbutyric acid with an equivalent amount of 2-propylpentanoic acid, (1-propylbutyl)isocyanate was obtained.

EXAMPLE 2

Preparation of d,1-α-(tert-Butoxycarbonyl-amino) tricyclo{3.3.1.1$^{3,7}$}decane-1-acetic Acid Benzyl Ester (Boc-NH—(R,S)—CH(adamantyl)C(O)—OBzl)

Under an inert atmosphere, tricyclo{3.3.1.1$^{3,7}$}decane-1-acetic acid (Aldrich Chemical Company, Inc., Milwaukee, Wis., USA) was converted to its corresponding benzyl ester in a 98% yield by reacting the compound with benzyl bromide (1 molar equiv.) in the presence of 1,8-diazabicyclo{5.4.0}undec-7-ene (1 molar equiv.) in acetonitrile at 4°.

The latter benzyl ester was converted to the title compound by the following series of steps: Under an argon atmosphere, a 1.4M hexane solution of butyllithium (6.5 mL, 9.1 mmol) was added with stirring to a cooled (0°) solution of diisopropylamine (1.08 g, 1.50 mL, 10.7 mmol) in THF (15 mL). The resulting solution was stirred at 0° for 15 min and then it was added dropwise to a solution of the last mentioned benzyl ester (2.00 g, 7.04 mmol) in dry THF (15 mL) at −78°. The mixture was stirred at −20° for 30 min, and then cooled to −78°. A solution of 2,4,6-triisopropylbenzenesulfonyl azide (2.38 g, 7.69 mmol) in dry THF (15 mL) was added in one portion to the cooled mixture. The mixture was stirred at 20° for 15 min and then quenched with glacial acetic acid (2 mL). Thereafter, the mixture was stirred at 25° for 16 h. The solvent was removed under reduced pressure. The residue was dissolved in EtOAc. The solution was washed successively with 1.0N aqueous HCl, 10% aqueous NaHCO$_3$ and brine, dried (MgSO$_4$) and evaporated to dryness under reduced pressure. The residue was purified by chromatography (SiO$_2$, eluent: hexane-EtOAc, 99:1) to give d,1-α-azidotricyclo{3.3.1.1$^{3,7}$}decane-1-acetic acid benzyl ester (251 mg).

The latter compound was reduced with tin (II) chloride in MeOH according to the method of N. Maiti et al., Tetrahedron Letters, 27, 1423 (1986) to give d,1-α-aminotricyclo{3.3.1.1$^{3,7}$}decane-1-acetic acid benzyl ester. Subsequent reaction of the latter amino acid benzyl ester with di-tert-butyl dicarbonate (1.05 molar equiv.) and triethylamine (1.05 equiv.) in dry THF under an argon atmosphere at 4° C. for 15 min and then at room temperature for 4 h, followed by the usual workup (cf section (b) of example 6 hereinafter), gave the title compound. H$^1$ NMR (CDCl$_3$) δ1.45 (s,9H), 1.5–2.0 (m,15H), 4.05 (d, J=9 Hz, 1H), 5.12 (d, J=9 Hz, 1H), 5.18 (m, 2H), 7.38 (m, 5H).

EXAMPLE 3

Preparation of the Intermediate Boc-Asp (pyrrolidino)-OH

N,N'-Carbonyldiimidazole (24.32 g, 0.15 mol) was added in small portions to a stirred solution of Boc-Asp-OBzl (47.60 g, 0.147 mol) in acetonitrile (500 mL). After 45 min, the reaction mixture was cooled to 0° and pyrrolidine (13.4 mL, 0.16 mol) was added dropwise. Thereafter, the mixture was stirred at room temperature to complete the reaction (about 3 h as judged by TLC). The solvent was removed under reduced pressure and the residue was dissolved in EtOAc (500 mL). The organic phase was washed with 10% aqueous HCl (3×100 mL), 1N aqueous NaOH (2×100 mL) and dried (MgSO$_4$). Evaporation of the organic phase under reduced pressure gave a colorless oil which solidified on standing. The latter product in a solution of EtOH (200 mL) was subjected to hydrogenolysis for 20 h at atmospheric pressure using 200 mg of 20% by weight of Pd(OH)$_2$ on carbon as the catalyst. The reaction mixture was filtered through diatomaceous earth. Evaporation of the filtrate afforded a residue which was purified by recrystallization from hexane/Et$_2$O to give the desired product (37.10 g, 88%), mp 114°–116°. The structure of the product was confirmed by NMR.

Corresponding N-substituted asparagine analogs can be obtained by replacing pyrrolidine in the procedure of this example with the appropriate amine (e.g. diethylamine or morpholine).

EXAMPLE 4

Preparation of the Intermediate Boc-2(S)-Amino-5-cyclopentyl-4-oxopentanoic Acid Boc-2(S)-amino-4-keto-1,6-hexanedioic acid 1-benzyl ester 6-(4-nitrophenyl)methyl ester (4.8 g, 9.6 mmol) was dissolved in DMF (100 mL). Na$_2$CO$_3$ (4.07 g, 38.4 mmol) and 1,4-diiodobutane (3.59 g, 11.6 mmol) were added to the solution. The mixture was stirred 18 h at room temperature and then heated at 50° for 3 h. Evaporation of the solvent, dissolution of the resulting residue with EtOAc, washing of the resulting solution with 1N aqueous HCl and water, followed by drying (MgSO$_4$) and evaporation gave a crude product. The crude product was purified by chromatography {SiO$_2$, eluent: hexane-EtOAc (4:1)} to give the corresponding benzyl ester of the title compound (4.3 g). The benzyl ester was subjected to hydrogenolysis {20% Pd(OH)$_2$)/C in MeOH, 18 h} and worked up (see section (d) of example 8 hereinafter) to give the title compound (140 mg). NMR and mass spectrum of the product were in agreement with the expected structure.

Analogous derived amino acid intermediates having a ketone in their side chain were prepared in a similar manner as described for this example using the appropriate alkyl iodide.

EXAMPLE 5

Preparation of 3-Alkyl- or 3,3-Dialkyl-L-aspartic Acid Intermediates and 2(S)-Amino-3-(1-carboxycycloalkyl)acetic Acid Intermediates These intermediates, which can be used to prepare compounds of formula 1 in which R$^2$ and R$^3$ are as defined herein, can be prepared according to the method of M. Bochenska and J. F. Biernat, Rocz. Chem., 50, 1195 (1976); see Chem. Abstr., 86, 43990r (1977).

For example, (±)-Boc-Asp(cyPn)(OBzl)-OH was prepared as follows: Sodium hydride (4.5 g, 60% dispersion in mineral oil, 122 mmol) was added in small portions over 5 h to a solution of (1-bromocyclopentane)carboxylic acid ethyl ester {17.1 g, 77.3 mmol, described by D. N. Harpp et al., J. Org. Chem., 46, 3420 (1975)} and freshly distilled ethyl isocyanoacetate (12.7 g, 122 mmol) in a mixture of dimethylsulfoxide and Et$_2$O (1:1, 120 mL). The resulting red slurry was stirred at room temperature for 16 h after which time it was treated with a saturated aqueous solution of ammonium chloride (5 mL). The resulting mixture was diluted with water (500 mL) and extracted (2×) with EtOAc. The EtOAc layers were combined and washed with water (2×) and then with brine. Drying (MgSO$_4$), filtering and concentration of the extract afforded a dark red oil. This material was subjected to flash chromatography through a 5×25 cm column of silica gel (eluent: EtOAc-hexane, 1:10). Concentration of the appropriate fractions provided α-cyano-1-carboxycyclopentaneacetic acid diethyl ester as a clear colorless viscous liquid (13 g, 66%).

The latter compound (13 g, 51 mmol) was mixed with 6N aqueous HCl (60 mL) at 0°. After dissolution, the reaction mixture was heated in a oil bath at 120° for 24 h. After this time, water was removed from the mixture using a dry ice rotary evaporator. The resulting white solid was dried under high vacuum for 18 h. The dried material was dissolved in a mixture of dioxane (50 mL) and 3N aqueous NaOH (52 mL). A solution of di(tertiarybutyl) dicarbonate (14.6 g, 67 mmol) in dioxane (25 mL) was added to the solution. The mixture was stirred at room temperature for 16 h. Additional 3N aqueous NaOH was added at intervals to keep the pH of the mixture at about 10. The mixture was diluted with water (500 mL) and extracted (2×) with Et$_2$O (200 mL). The aqueous phase was rendered acidic (pH=3) with solid citric acid and extracted with EtOAc (2×300 mL). The combined EtOAc extracts were washed with water (3×) and brine. Drying, filtering and concentration of the extract afforded Boc-Asp(cyPn)-OH as a white solid (14 g, 96%).

To a solution of the latter compound (7.2 g, 25 mmol) in dry DMF (50 mL) was added K$_2$CO$_3$ (7.6 g, 55 mmol) and benzyl bromide (6.6 mL, 55 mmol). The reaction mixture was stirred at room temperature for about 7 h. Thereafter, the reaction mixture was poured into a mixture of water (500 mL) and EtOAc (350 mL). The organic phase was washed with water (2×) and brine. Drying, filtering and concentration of the extract provided a pale yellow viscous liquid. This material was subjected to flash chromatography (SiO$_2$, eluent: hexane-EtOAc, 12:1). Concentration of the appropriate fractions provided the dibenzyl derivative of Boc-Asp-(cyPn)-OH as a low melting white solid (11 g, 94%). The dibenzyl product was dissolved in tetrahydrofuran (100 mL) and an aqueous solution of LiOH (23.5 mL, 1N) was added. After 4 h, the reaction mixture was poured into water and extracted with Et$_2$O (3×). The aqueous phase was rendered acidic with 10% aqueous citric acid and extracted with EtOAc (2×). The EtOAc layers were combined, dried ($MgSO_4$), filtered and concentrated to provide (+)-Boc-Asp(cyPn)(OBzl)-OH as a clear colorless gum (7.3 g, 82%).

EXAMPLE 6

General Procedure for Coupling Reactions
{See also R. Knorr et al., Tetrahedron Letters, 30, 1927 (1989).}

The first reactant, i.e. a free amine (or its hydrochloride salt), is dissolved in $CH_2Cl_2$ or acetonitrile and the solution is cooled to 4°. Under a nitrogen atmosphere, four equivalents of N-methylmorpholine is added to the stirred solution. After 20 min., one equivalent of the second reactant, i.e. a free carboxylic acid, and 1.05 equivalent of the coupling agent are added. (Practical and efficient coupling reagents for this purpose are (benzotriazol-1-yloxy)tris-(dimethylamino)phosphonium hexafluorophosphate or preferably 2-(1H-benzotriazol-1-yl)-N,N,N',N'-tetramethyluronium tetrafluoroborate. The reaction is monitored by TLC. After completion of the reaction, the $CH_2Cl_2$ (or acetonitrile) is evaporated under reduced pressure. The residue is dissolved in EtOAc. The solution is washed successively with 1N aqueous citric acid, 10% aqueous $Na_2CO_3$ and brine. The organic phase is dried ($MgSO_4$), filtered and concentrated to dryness under reduced pressure. The residue is purified on silica gel ($SiO_2$) according to Still's flash chromatography technique {W. C. Still et al., J. Org. Chem., 43, 2923 (1978)}.

EXAMPLE 7

Preparation of the Intermediate H-Asp(cyPn)(Bzl)-NH-(S)-CH{$CH_2C(CH_3)_3$}$CH_2OBzl$ (a) (S)-α-Azido-1-{(phenylmethoxy)carbonyl}-cyclopentaneacetic acid: This compound was prepared from 2-oxaspira{4.4}nonane-1,3-dione, described by M. N. Aboul-Enein et al., Pharm. Acta Helv., 55, 50 (1980), according to the asymmetric azidation method utilizing the Evan's auxiliary, see D. A. Evans et al., J. Amer. Chem. Soc., 112, 4011 (1990). The $^1$H NMR ($CDCl_3$) of the compound showed: δ4.55 (s,1H), 5.12 (s,2H) and 7.4 (m,5H). The compound is used in section (c) of this example.

(b) $NH_2$—(S)—CH{$CH_2C(CH_3)_3$}$CH_2OBzl$: H-γMeLeu-OH was reduced with $LiBH_4/Me_3SiCl$ according to the method of A. Giannis and K. Sandhoff, Angew. Chem. Int. Ed. Engl., 28, 218 (1989) to give the aminoalcohol $NH_2$—(S)—CH{$CH_2C(CH_3)_3$}$CH_2OH$. A mixture of the latter compound (812 mg, 6.2 mmol), triethylamine (659 mg, 6.51 mmol) and di-tert-butyl carbonate (1.42 g, 6.51 mmol) in dry THF (15 mL) was stirred under a nitrogen atmosphere at 4° for 15 min and then at room temperature for 4 h. The THF was evaporated under reduced pressure. The residue was dissolved in EtOAc. The solution was washed with 10% aqueous citric acid, 5% aqueous $NaHCO_3$ and brine. The organic phase was dried ($MgSO_4$) and concentrated to dryness under reduced pressure. The residue was purified by flash chromatography ($SiO_2$, eluent: hexane-EtOAc, 2:1) to give Boc-NH-(S)-CH{$CH_2C$—$(CH_3)_3$}$CH_2OH$.

Tetrabutylammonium bisulfate (106 mg) and 50% aqueous NaOH (3 mL) were added successively to a solution of Boc-NH—(S)—CH{$CH_2C(CH_3)_3$}$CH_2OH$ in benzyl chloride (13 mL). The resulting mixture was stirred at 35°–40° for 90 min, diluted with EtOAc, and washed with $H_2O$ and brine. The organic phase was dried ($MgSO_4$) and concentrated to dryness under reduced pressure. The residue was dissolved in hexane. The solution was poured onto a column of $SiO_2$. The column was eluted with hexane to remove benzyl chloride, and then with hexane-EtOAc (2:1) to give Boc-NH—(S)—CH{$CH_2C(CH_3)$}$CH_2OBzl$. The $^1$H NMR ($CDCl_3$) of the latter compound showed δ1.0 (s,9H), 1.42 (s, 10H), 3.42 (d, J=4 Hz, 2H), 3.88 (broad, 1H), 4.54 (t, 3H), 7.23–7.4 (m, 5H). The latter compound (1.28 g, 3.99 mmol) was dissolved in 6N HCl/dioxane (10 mL). The solution was stirred under a nitrogen atmosphere at 40 for 45 min. Evaporation of the solvent gave the hydrogen chloride salt of the desired compound (1.05 g). The compound is used without further purification in the next section of this example.

(c) The title compound of this example: By following the coupling procedure of example 6 and using the hydrogen chloride salt of $NH_2$—(S)—CH{$CH_2C(CH_3)_3$}$CH_2OBzl$ of the preceding section as the first reactant and (S)-α-azido-1-{(phenylmethoxy)carbonyl}cyclopentaneacetic acid of section (a) of this example as the second reactant, N—{(S)-1-benzyloxymethyl-3,3-dimethylbutyl}-(S)-α-azido-1-{(phenylmethoxy)carbonyl}cyclopentaneacetamide was obtained. Reduction of the latter compound with tin(II) chloride in MeOH according to the method of N. Maiti et al., Tetrahedron Letters, 27, 1423 (1986) gave the title compound of this example. The $^1$H NMR ($CDCl_3$) of the compound showed δ0.98 (s, 9H), 1.22–1.9 (m, 2H), 3.4 (d, J=4 Hz, 2H), 3.64 (s, 1H), 4.18 (broad m, 1H), 4.52 (s, 2H), 5.12 (s, 2H), 7.1–7.38 (broad m, 10H).

EXAMPLE 8

Preparation of $Pr_2CHNHC(O)$-Tbg-Asp(pyrrolidino)-Asp(cyPn)-γMeLeucinol (a) Boc-Tbg-OH (7.5 g, 32,5 mmol) was converted to its corresponding benzyl ester in an 85% yield by reacting the compound with benzyl bromide (1.2 molar equiv.) in the presence of 1,8-diazabicyclo-{5.4.0}undec-7-ene in acetonitrile under an argon atmosphere at room temperature for 16 h. Isolation of the product by routine procedure and purification by flash chromatography ($SiO_2$, eluent: hexane-EtOAc, 9:1) gave the benzyl ester as a colorless oil (8.83 g, 85%).

(b) A solution of the latter ester (242 mg, 0.75 mmol) in 6.3N HCl/dioxane (4 mL) was stirred under an $N_2$ atmosphere at 0° for 45 min and then concentrated under reduced pressure to give the corresponding N-deprotected amino acid derivative, H-Tbg-OBzl, in the form of its hydrochloride salt.

(c) A solution of the latter salt (7.71 g, 30 mmol) and triethylamine (6.5 g, 9.06 mL, 65 mmol) was stirred at 0° for 5 min. A solution of (1-propylbutyl)isocyanate (65 mmol) in toluene (conc.=250 mg/mL, see example 1 for preparation) was added. Thereafter, the reaction mixture was stirred at room temperature for 16 h. The reaction mixture was concentrated under reduced pressure. The residue was dissolved in EtOAc. The solution was washed with 1M aqueous HCl, 5% aqueous $Na_2CO_3$ and brine, dried ($MgSO_4$) and evaporated to dryness under reduced pressure. The residue was purified by flash chromatography ($SiO_2$, eluent: hexane-EtOAc, 4:1) to give $Pr_2CHNHC(O)$-Tbg-OBzl (8.33 g, 76%).

(d) The latter compound (8.33 g, 23 mmol) was subjected to hydrogenolysis (10% Pd/C, EtOH, 1 atmosphere of hydrogen, 4 h). After completion of the reaction, the catalyst was removed by filtration through a 45 µm membrane and the filtrate was concentrated under reduced pressure to give Pr₂CHNHC(O)-Tbg-OH as a white solid (5,94 g, 95%).

(e) By following the coupling procedure of example 6 and using H-Asp(cyPn)(Bzl)-NH—(S)—CH{CH₂C(CH₃)₃}CH₂OBzl of example 7 as the first reactant and Boc-Asp(pyrrolidino)-OH of example 3 as the second reactant, Boc-Asp(pyrrolidino)-Asn(cyPn)(Bzl)-NH—(S)—CH{CH₂C(CH₃)₃}CH₂OBzl was obtained. Deprotection of the latter compound according to the procedure of section (b) of this example gave H-Asp(pyrrolidino)-Asp(cyPn)(Bzl)-NH—(S)—CH{CH₂C(CH₃)₃}CH₂OBzl.

(f) By following the coupling procedure of example 6 and using the latter compound as the first reactant and Pr₂CHNHC(O)-Tbg-OH of section (d) of this example as the second reactant, Pr₂CHNHC(O)-Tbg-Asp(pyrrolidino)-Asp(cyPn)(Bzl)-NH—(S)—CH{CH₂C(CH₃)₃}CH₂OBzl was obtained.

(g) The latter compound (102 mg, 0.11 mmol) was subjected to hydrogenolysis (10% Pd/C, MeOH, 1 atmosphere of hydrogen, 1 h). After completion of the reaction, the catalyst was removed by filtration through a 45 µm membrane and the filtrate was concentrated under reduced pressure to give the title compound as a white solid (69 mg, 85%). $^1$NMR (DMSO-D$_6$) δ1.8 (2s, 18H), 1.1–2.0 (m, 28H), 2.6–3.8 (m, 12H), 4.1 (d, 1H), 4.6 (m, 1H), 4.9 (d, 1H), 5.9 (d, 1H), 5.95 (d, 1H), 7.60 (d, 1H), 8.1 (d, 1H), 8.4 (d, 1H). Mass spectrum: 723 (M+H)$^+$.

By using the appropriate intermediates, the serial coupling and the deprotection procedures of examples 6 to 8 can be used to prepare other compounds of formula 1, such as those exemplified in the table of the following example. In some cases, precipitation of the final product does not afford pure material. In those instances, the product can be purified by semipreparative HPLC on a C-18 reversed-phase column using a gradient of acetonitrile and H₂O, each of the latter solvents containing 0.06% TFA. To this end, the crude product was dissolved in 0.1M aqueous NH₄OH and the pH of the solution was brought back to about 7 using 0.1M aquous AcOH, prior to purification. When applicable, diastereoisomeric mixtures were separated in this fashion.

EXAMPLE 9

Inhibition of Herpes Simplex Virus (HSV-1) Ribonucleotide Reductase a) Preparation of Enzyme HSV-1 ribonucleotide reductase (partially purified) was obtained from quiescent BHK-21/C13 cells infected with strain F HSV-1 virus at 10 plaque forming units/cell as described by E. A. Cohen et al., J. Gen. Virol., 66, 733 (1985).

b) Assay and Results for Exemplified Peptides

By following the procedure described by P. Gaudreau et al., J. Biol, Chem., 262, 12413 (1987), the assay results listed in the following table were obtained. The assay result for each exemplified compound of formula 1 is expressed as the concentration of the compound producing 50% of the maximal inhibition (IC$_{50}$) of enzyme activity. The number of units of the enzyme preparation used in each assay was constant, based on the specific activity of the enzyme preparation. The results are relative to the activity obtained in control experiments without the test compound and represent the mean of four assays that varied less than 10% with each other.

TABLE

| Compound of Formula 1 | FAB/MS (M + Na)$^+$ | IC$_{50}$ µM |
|---|---|---|
| Title Compound of Example 8 | 723* | 0.08 |
| Et₂CHNHC(O)-Tbg-Asp(pyrrolidino)-Asp(cyPn)-γMeLeu-OH | 731 | 0.10 |
| Et₂CHNHC(O)-Tbg-Asp(pyrrolidino)-Asp(cyPn)-γMeLeucinol | 717 | 0.098 |
| MeNHC(O)-Tbg-Asp(pyrrolidino)-Asp(cyPn)-γMeLeucinol | 661 | 0.89 |
| Me₂CHNC(O)-Tbg-Asp(pyrrolidino)-Asp(cyPn)-γMeLeucinol | 689 | 0.07 |
| PhNHC(O)-Tbg-Asp(pyrrolidino)-Asp(cyPn)-γMeLeucinol | 723 | 0.71 |
| BzlNHC(O)-Tbg-Asp(pyrrolidino)-Asp(cyPn)-γMeLeucinol | 715* | 0.41 |
| Et₂CHNHC(O)-Tbg-Asp(pyrrolidino)-Asp(cyPn)-NHCH₂CH₂CMe₃ | 687 | 0.20 |
| Me₃CNHC(O)-Tbg-Asp(pyrrolidino)-Asp(cyPn)-γMeLeucinol | 681* | 0.10 |
| Et₂CHNHC(O)—NH-(S)-CH(adamantyl)-C(O)-Asp(pyrrolidino)-Asp(cyPn)-γMeLeu-OH | 787* | 0.082 |
| Et₂CHNHC(O)—NH-(S)-CH(adamantyl)-C(O)-Asp(pyrrolidino)-Asp(cyPn)-γMeLeucinol | 795 | 0.16 |
| Et₂CHNHC(O)-Tbg-Asp(pyrrolidino)-Asp{(R)-iPr}-Leu-OH | 705 | 0.57 |
| Et₂CHNHC(O)-Tbg-Asp(pyrrolidino)-Asp(cyPn)-NHCH₂CMe₃ | 651* | 0.13 |
| Et₂CHNHC(O)-Tbg-Asp(pyrrolidino)-Asp{(R)-iPr}-γMeLeucinol | 705 | 0.10 |
| Et₂CHNHC(O)-Tbg-Asp(pyrrolidino)-Asp{(R)-iPr}-γMeLeu-OH | 697* | 0.072 |
| Et₂CHNHC(O)-Tbg-Asp(pyrrolidino)-Asp(cyPn)-NHCH₂CHMe₂ | 637* | 0.60 |
| Pr₂CHNHC(O)-Tbg-Asp(pyrrolidino)-Asp(cyPn)-γMeLeu-OH | 737* | 0.096 |
| Pr₂CHNHC(O)-Tbg-Asp(pyrrolidino)-Asp(cyPn)-NHCH₂CMe₃ | 679* | 0.18 |
| (1-propylcyclopentyl)-NHC(O)-Tbg-Asp(pyrrolidino)-Asp(cyPn)-γMeLeu-OEt | 799 | 0.2 |
| Pr₂CHNHC(O)-Asp(diMe)-Asp(pyrrolidino)-Asp(cyPn)-γMeLeucinol | 753* | 0.2 |
| Pr₂CHNHC(O)-Tbg-Asp(pyrrolidino)-Asp(cyPn)-NHCH(CH₃)CMe₃ | 715 | 0.18 |
| Pr₂CHNHC(O)-Tbg-NHCH(3-ethyl-2-oxopentyl)CO-Asp(cyPn)-NHCH₂CMe₃ | 702 | 0.4 |
| Pr₂CHNHC(O)-Tbg-NHCH(2-cyclohexyl-2-oxoethyl)C(O)-Asp(cyPn)-NHCH₂CMe₃ | 714 | 0.14 |
| Pr₂CHNHC(O)-Tbg-NH-(S)-CH(2-cyclopentyl-2-oxoethyl)C(O)-Asp(cyPn)-NHCH₂CMe₃ | 700 | 0.20 |
| Pr₂CHNHC(O)—NH-(S)-CH{C(CH₃)₂OH}—C(O)-Asp(pyrrolidino)-Asp(cyPn)γMeLeucinol | 761 | 0.1 |
| Pr₂CHNHC(O)—NH-(R)-CH{C(CH₃)₂SH}CO-Asp(pyrrolidino)-Asp(cyPn)-γMeLeucinol | 777 | 0.15 |
| PrMe₂CNHC(O)-Tbg-Asp(pyrrolidino)-Asp(cyPn)-γMeLeu-OH | 723* | 0.10 |
| (1-propylcyclopentyl)-NHC(O)-Tbg-Asp(pyrrolidino)-Asp(cyPn)-γMeLeu-OH | 771 | 0.13 |
| Pr₂CHNHC(O)-Tbg-NH-(S)-CH(2-cyclobutyl-2-oxoethyl)C(O)-Asp(cyPn)-NHCH₂CMe₃ | 686 | 0.25 |
| Me₃CCH₂CMe₂HNC(O)-Tbg-Asp-(pyrrolidino)-Asp(cyPn)-γMeLeu-OH | 773 | 0.18 |
| Pr₂CHNHC(O)-Tbg-Asp(pyrrolidino)- | | |

TABLE-continued

| Compound of Formula 1 | FAB/MS (M + Na)+ | IC$_{50}$ μM |
|---|---|---|
| Asp(cyPn)-NHCH$_2$CMe$_2$Et | 693* | 0.24 |
| MePr$_2$CNHC(O)-Tbg-Asp(pyrrolidino)-Asp(cyPn)-NHCH$_2$CMe$_3$ | 693* | 0.16 |
| EtPr$_2$CNHC(O)-Tbg-Asp(pyrrolidino)Asp(cyPn)-NH-(R)-CH(Et)CMe$_3$ | 735* | 0.14 |

*FAB/MS (M + H)+

EXAMPLE 10

Inhibition of Herpes Simplex Virus (HSV-2) Replication in Cell Culture

Assay:

BHK-21/C13 cells (ATCC CCL 10) are incubated for two days in 150 cm$^2$ T-flasks (1.5×10$^6$ cells/flask) with alpha-MEM medium (Gibco Canada Inc., Burlington, Ontario, Canada) supplemented with 8% (v/v) fetal bovine serum (FBS, Gibco Canada Inc.). The cells are trypsinized and then transferred to fresh media in a 24 well plate to give 2.5×10$^5$ cells in 750 μL of media per well. The cells are incubated at 37° for a period of 6 h to allow them to adhere to the plate. Thereafter, the cells are washed once with 500 μL of alpha-MEM supplemented with 0.5% (v/v) FBS and then incubated with 750 μL of the same media (low serum) for 3 days. After this period of serum starvation, the low serum medium is removed and the cells are incubated in 500 μL of BBMT for 2 to 3 hours. {BBMT medium is described by P. Brazeau et al., Proc. Natl. Acad. Sci. USA, 79, 7909 (1982).} Thereafter, the cells are infected with HSV-2 (multiplicity of infection=0.02 PFU/cell) in 100 μL of BBMT medium. (Note: The HSV-2 used was strain HG-52, see Y. Langelier and G. Buttin, J. Gen. Virol., 57, 21 (1981); the virus was stored at −80°.) Following 1 h of virus adsorption at 37°, the media is removed and the cells are washed with BBMT (3×250 μL). The cells in each well are incubated with or without (control) appropriate concentrations of the test agent dissolved in 200 μL of BBMT medium. After 29 h of incubation at 37°, the infected cells are harvested by first freezing the plate at −80°, followed by thawing. The cells in each well are scraped off the surface of the well with the help of the melting ice fragments. After complete thawing, the cell suspensions are collected and each well is rinsed with 150 μL of BBMT medium. The viral sample (suspension plus washing) is sonicated gently for 4 min at 4°. Cell debris are removed by centrifugation (1000 times gravity for 10 minutes at 4°). The supernatant is collected and stored at −80° until determination of viral titer.

Viral titration was performed by a modification of the colorimetric assay method of M. Langlois et al., Journal of Biological Standardization, 14, 201 (1986).

More specifically, in a similar manner as described above, BHK-21/C13 cells are trypsinized and transferred to fresh media in a 96 well microtiter plate to give 20,000 cells in 100 μL of media per well. The cells in the prepared plate are incubated at 37° for 2 h. During that time, the viral sample is thawed and sonicated gently for 15 seconds, and log dilutions of the sample are prepared (1/5 sequential: 50 μL of the sample plus 200 μL of BBMT medium, sequential dilutions being done with a multichannel pipette.

On completion of the above 2 hour incubation of the BHK-21/C13 cells, the media is replaced with alpha-MEM medium supplemented with 3% (v/v) FBS. The cells are now ready to be infected with the various sample dilutions of virus. Aliquots (50 μL) of the various dilutions are transferred into the appropriate wells of the plate. The resulting infected cells are incubated for 2 days at 37°. Then 50 μL of a 0.15% (v/v) solution of neutral red dye in Hank's Balanced Salt Solution (pH 7.3, Gibco Canada Inc.) is added to each well. The prepared plate is incubated for 45 min at 37°. Medium from each well is then aspirated and the cells are washed once with 200 μL of Hank's Balanced Salt Solution. After the wash, the dye is released from the cells by the addition of 100 μL of a 1:1 mixture of 0.1M Sorensen's citrate buffer (pH 4.2) and ethanol. {Sorensen's citrate buffer is prepared as follows: Firstly, a 0.1M disodium citrate solution is prepared by dissolving citric acid monohydrate (21 g) in 1N aqueous NaOH (200 mL) and adding sufficient filtered H$_2$O to make 1 L. Secondly, the 0.1M disodium citrate solution (61.2 mL) is mixed with 0.1N aqueous HCl (38.8 mL) and the pH of the resulting solution is adjusted to 4.2 if necessary.} The mixture in the wells is subjected to a gentle vortex action to ensure proper mixing. The plate wells are scanned by a spectrophotometer plate reader at 540 μm to assess the number of viable cells. In this manner, the percentage of virus growth inhibition can be determined for the various concentrations of the test agent, and the concentration of the test agent effecting a 50% inhibition of virus replication, i.e. the EC$_{50}$ can be calculated.

Results:

The following table provides examples of the results obtained when peptides of formula 1 were evaluated according to the cell culture assay of this example.

TABLE

| Compound of Formula 1 | EC$_{50}$ μM |
|---|---|
| Title Compound of Example 8 | 75 |
| Et$_2$CHNHC(O)-Tbg-Asp(pyrrolidino)-Asp(cyPn)-γMeLeu-OH | 180 |
| Et$_2$CHNHCO-Tbg-Asp(pyrrolidino)-Asp(cyPn)-γMeLeucinol | 170 |
| Me$_2$CHNHC(O)-Tbg-Asp(pyrrolidino)-Asp(cyPn)-γMeLeucinol | 700 |
| Et$_2$CHNHC(O)-Tbg-Asp(pyrrolidino)-Asp(cyPn)-NHCH$_2$CH$_2$CMe$_3$ | 350 |
| Me$_3$CNHC(O)-Tbg-Asp(pyrrolidino)-Asp(cyPn)-γMeLeucinol | 300 |
| Et$_2$CHNHC(O)—NH-(S)-CH(adamantyl)-C(O)-Asp(pyrrolidino)-Asp(cyPn)-γMeLeu-OH | 170 |
| Et$_2$CHNHC(O)—NH-(S)-CH(adamantyl)-C(O)-Asp(pyrrolidino)-Asp(cyPn)-γMeLeucinol | 170 |
| Et$_2$CHNHC(O)-Tbg-Asp(pyrrolidino)-Asp{(R)-iPr}-Leu-OH | 300 |
| Et$_2$CHNHC(O)-Tbg-Asp(pyrrolidino)-Asp(cyPn)-NHCH$_2$CMe$_3$ | 270 |
| Et$_2$CHNHC(O)-Tbg-Asp(pyrrolidino)-Asp{(R)-iPr}-γMeLeucinol | 140 |
| Et$_2$CHNHC(O)-Tbg-Asp(pyrrolidino)-Asp{(R)-iPr}-γMeLeu-OH | 190 |
| Pr$_2$CHNHC(O)-Tbg-Asp(pyrrolidino)-Asp(cyPn)-γMeLeu-OH | 80 |
| Pr$_2$CHNHC(O)-Tbg-Asp(pyrrolidino)-Asp(cyPn)-NHCH$_2$CMe$_3$ | 150 |
| (1-propylcyclopentyl)-NHC(O)-Tbg-Asp(pyrrolidino)-Asp(cyPn)-γMeLeu-OEt | 45 |
| Pr$_2$CHNHC(O)-Asp(diMe)-Asp(pyrrolidino)-Asp(cyPn)-γMeLeucinol | 170 |
| Pr$_2$CHNHC(O)-Tbg-Asp(pyrrolidino)-Asp(cyPn)-NHCH-(R)-CH(Me)CMe$_3$ | 55 |
| Pr$_2$CHNHC(O)-Tbg-NHCH(3-ethyl-2-oxopentyl)CO-Asp(cyPn)-NHCH$_2$CMe$_3$ | 25 |
| Pr$_2$CHNHC(O)-Tbg-NHCH(2-cyclohexyl- | 140 |

TABLE-continued

| Compound of Formula 1 | EC$_{50}$ μM |
|---|---|
| 2-oxoethyl)C(O)-Asp(cyPn)-NHCH$_2$CMe$_3$ | |
| Pr$_2$CHNHC(O)-Tbg-NHCH(2-cyclopentyl-2-oxoethyl)C(O)-Asp(cyPn)-NHCH$_2$CMe$_3$ | 90 |
| Pr$_2$CHNHC(O)—NH-(S)-CH{C(CH$_3$)$_2$OH}—C(O)-Asp(pyrrolidino)-Asp(cyPn) γMeLeucinol | 210 |
| Pr$_2$CHNHC(O)—NH-(R)-CH{C(CH$_3$)$_2$SH}CO-Asp(pyrrolidino)-Asp(cyPn)-γMeLeucinol | 290 |
| PrMe$_2$CNHC(O)-Tbg-Asp(pyrrolidino)-Asp(cyPn)-γMeLeu-OH | 110 |
| (1-propylcyclopentyl)NHCO-Tbg-Asp-(pyrrolidino)-Asp(cyPn)-γMeLeu-OH | 190 |
| Pr$_2$CHNHC(O)-Tbg-NH-(S)-CH(2-cyclobutyl-2-oxoethyl)C(O)-Asp(cyPn)-NHCH$_2$CMe$_3$ | 160 |
| Me$_3$CCH$_2$CMe$_2$NHC(O)-Tbg-Asp(pyrrolidino)-Asp(cyPn)-γMeLeu-OH | 110 |
| Pr$_2$CHNHC(O)-Tbg-Asp(pyrrolidino)-Asp(cyPn)-NHCH$_2$CMe$_2$Et | 106 |

TABLE-continued

| Compound of Formula 1 | EC$_{50}$ μM |
|---|---|
| MePr$_2$CNHC(O)-Tbg-Asp(pyrrolidino)-Asp(cyPn)NHCH$_2$CMe$_3$ | 84 |
| EtPr$_2$CNHC(O)-Tbg-Asp(pyrrolidino)-Asp(cyPn)NH-(R)-CH(Et)CMe$_3$ | 7 |

Other compounds of formula 1 include:

Pr$_2$CHNHC(O)-Tbg-Asp(pyrrolidino)-Asp(cyPn)-NH-(R)-CH(Et)CMe$_3$

MePr$_2$CNHC(O)-Tbg-Asp(pyrrolidino)-Asp(cyPn)NH-(R)-CH(Me)CH$_2$CMe$_3$

EtPr$_2$CNHC(O)-Tbg-Asp(pyrrolidino)-Asp(cyPn)-NH-(R)-CH(Me)CH$_2$CMe$_3$

MePr$_2$CNHC(O)-Tbg-Asp(pyrrolidino)-Asp(cyPn)-NH-(R)-CH(Et)CH$_2$CMe$_3$

EtPr$_2$CNHC(O)-Tbg-Asp(pyrrolidino)-Asp(cyPn)-NH-(R)-CH(Et)CH$_2$CMe$_3$

---

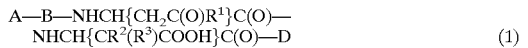

We claim:

1. A peptide of formula 1

$$A-B-NHCH\{CH_2C(O)R^1\}C(O)-NHCH\{CR^2(R^3)COOH\}C(O)-D \qquad (1)$$

wherein A is (1-methylethyl)aminocarbonyl, (1,1-dimethylethyl)aminocarbonyl, (1-ethylpropyl)aminocarbonyl, (1,1-dimethylbutyl)aminocarbonyl, (1,1,3,3-tetramethylbutyl)aminocarbonyl, (1-propylbutyl)aminocarbonyl, 1-methyl-1-propylbutylaminocarbonyl, 1-ethyl-1-propylbutylaminocarbonyl or (1-propylcyclopentyl)aminocarbonyl; B is an amino acid residue of (S)-α-aminotricylo$\{3.3.1.1^{3,7}\}$decane-1-acetic acid, (S)-2-amino-3-hydroxy-3-methylbutanoic acid or (R)-2-amino-3-mercapto-3-methylbutanoic acid, or an amino acid residue selected from Tbg and Asp(diMe); $R^1$ is 2-ethylpropyl, cyclopentyl, cyclohexyl or pyrrolidino; $R^2$ is hydrogen and $R^3$ is 1-methylethyl and the carbon atom bearing $R^2$ and $R^3$ has the (R)-configuration, or $R^2$ and $R^3$ together with the carbon atom to which they are attached form a cyclopentyl; and D is $NHR^8$ wherein $R^8$ is 2-methylpropyl, 2,2-dimethylpropyl, 1(R),2,2-trimethylpropyl, 1(R)-ethyl-2,2-dimethylpropyl, 2,2-dimethylbutyl or 3,3-dimethylbutyl, or D is $NHCH(R^9)-Z$ wherein the carbon atom bearing $R^9$ has the (S)-configuration, $R^9$ is 2-methylpropyl or 2,2-dimethylpropyl and Z is $CH_2OH$, C(O)OH or $C(O)OR^{10}$ wherein $R^{10}$ is methyl; or a therapeutically acceptable salt thereof.

2. A peptide as defined in claim 1 wherein A is (1-methylethyl)aminocarbonyl, (1,1-dimethylethyl)aminocarbonyl, (1-ethylpropyl)aminocarbonyl, (1-propylbutyl)amino-carbonyl, 1-methyl-1-propylbutylaminocarbonyl, 1-ethyl-1-propylbutylaminocarbonyl or (1-propylcyclopentyl)aminocarbonyl; B, $R^1$, $R^2$ and $R^3$ are as defined in claim 1; and D is $NHR^8$ wherein $R^8$ is 2,2-dimethylpropyl, 1(R),2,2-trimethylpropyl, 1(R)-ethyl-2,2-dimethylpropyl, 2,2-dimethylbutyl or 3,3-dimethylbutyl, or D is $NHCH(R^9)-Z$ wherein the carbon atom bearing $R^9$ has the (S)-configuration, $R^9$ is 2,2-dimethylpropyl and Z is $CH_2OH$, C(O)OH or $C(O)OR^{10}$ wherein $R^{10}$ is methyl; or a therapeutically acceptable salt thereof.

3. A peptide as defined in claim 1 selected from the group consisting of:

Pr$_2$CHNHC(O)-Tbg-Asp(pyrrolidino)-Asp(cyPn)-γMeLeucinol,
Et$_2$CHNHC(O)-Tbg-Asp(pyrrolidino)-Asp(cyPn)-γMeLeu-OH,
Et$_2$CHNHCO-Tbg-Asp(pyrrolidino)-Asp(cyPn)-γMeLeucinol,
Et$_2$CHNHC(O)-Tbg-Asp(pyrrolidino)-Asp(cyPn)-NHCH$_2$CH$_2$CMe$_3$,
Me$_3$CNHC(O)-Tbg-Asp(pyrrolidino)-Asp(cyPn)-γMeLeucinol,
Et$_2$CHNHC(O)—NH—(S)—CH(adamantyl)-C(O)-Asp(pyrrolidino)-Asp(cyPn)-γMeLeu-OH,
Et$_2$CHNHC(O)—NH—(S)—CH(adamantyl)-C(O)-Asp(pyrrolidino)-Asp(cyPn)-γMeLeucinol,
Et$_2$CHNHC(O)-Tbg-Asp(pyrrolidino)-Asp$\{(R)$-iPr$\}$-Leu-OH,
Et$_2$CHNHC(O)-Tbg-Asp(pyrrolidino)-Asp(cyPn)-NHCH$_2$CMe$_3$,
Et$_2$CHNHC(O)-Tbg-Asp(pyrrolidino)-Asp$\{(R)$-iPr$\}$-γMeLeucinol,
Et$_2$CHNHC(O)-Tbg-Asp(pyrrolidino)-Asp$\{(R)$-iPr$\}$-γMeLeu-OH,
Et$_2$CHNHC(O)-Tbg-Asp(pyrrolidino)-Asp(cyPn)-NHCH$_2$CHMe$_2$,
Pr$_2$CHNHC(O)-Tbg-Asp(pyrrolidino)-Asp(cyPn)-γMeLeu-OH,
Pr$_2$CHNHC(O)-Tbg-Asp(pyrrolidino)-Asp(cyPn)-NHCH$_2$CMe$_3$,
(1-propylcyclopentyl)-NHC(O)-Tbg-Asp(pyrrolidino)-Asp(cyPn)-γMeLeu-OEt,
Pr$_2$CHNHC(O)-Asp(diMe)-Asp(pyrrolidino)-Asp(cyPn)-γMeLeucinol,
Pr$_2$CHNHC(O)-Tbg-Asp(pyrrolidino)-Asp(cyPn)-NH—(R)—CH(Me)CMe$_3$,
Pr$_2$CHNHC(O)-Tbg-NHCH(3-ethyl-2-oxopentyl)CO-Asp(cyPn)-NHCH$_2$CMe$_3$
Pr$_2$CHNHC(O)-Tbg-NHCH(2-cyclohexyl-2-oxoethyl)C(O)-Asp(cyPn)-NHCH$_2$CMe$_3$,
Pr$_2$CHNHC(O)-Tbg-NHCH(2-cyclopentyl-2-oxoethyl)C(O)-Asp(cyPn)-NHCH$_2$CMe$_3$,
Pr$_2$CHNHC(O)—NH—(S)—CH$\{C(CH_3)_2$OH$\}$C(O)-Asp(pyrrolidino)-Asp(cyPn)-γMeLeucinol,
Pr$_2$CHNHC(O)—NH—(R)—CH$\{C(CH_3)_2$SH$\}$CO-Asp(pyrrolidino)-Asp(cyPn)-γMeLeucinol,
PrMe$_2$CNHC(O)-Tbg-Asp(pyrrolidino)-Asp(cyPn)-γMeLeu-OH,
(1-propylcyclopentyl)NHCO-Tbg-Asp(pyrrolidino)-Asp(cyPn)-γMeLeu-OH,
Pr$_2$CHNHC(O)-Tbg-NH—(S)—CH(2-cyclobutyl-2-oxoethyl)-C(O)-Asp(cyPn)-NHCH$_2$CMe$_3$,
Me$_3$CCH$_2$CMe$_2$NHC(O)-Tbg-Asp(pyrrolidino)-Asp(cyPn)-γMeLeu-OH,
Pr$_2$CHNHC(O)-Tbg-Asp(pyrrolidino)-Asp(cyPn)-NHCH$_2$CMe$_2$Et,
MePr$_2$CNHC(O)-Tbg-Asp(pyrrolidino)-Asp(cyPn)-NHCH$_2$CMe$_3$, and MePr$_2$CNHC(O)-Tbg-Asp(pyrrolidino)-Asp(cyPn)NH—(R)—CH(Et)CH$_2$CMe$_3$.

4. A pharmaceutical composition comprising an anti-herpes virally effective amount of a peptide as defined in claim 1, or a therapeutically acceptable salt thereof, and a pharmaceutically or veterinarily acceptable carrier.

5. A method of treating a herpes viral infection in a mammal comprising administering to the mammal an anti-herpes virally effective amount of the peptide as defined in claim 1, or a therapeutically acceptable salt thereof.

6. A method of inhibiting the replication of herpes virus by contacting the virus with a herpes viral ribonucleotide reductase inhibiting amount of the peptide as defined in claim 1, or a therapeutically acceptable salt thereof.

7. A method of treating herpes simplex virus type 1, or type 2, infections in a mammal comprising administering thereto an effective amount of the pharmaceutical composition of claim 4 wherein the peptide of formula 1 of the composition is selected from the group consisting of:

Pr$_2$CHNHC(O)-Tbg-Asp(pyrrolidino)-Asp(cyPn)-γMeLeucinol,

Et$_2$CHNHC(O)-Tbg-Asp(pyrrolidino)-Asp(cyPn)-γMeLeu-OH,

Et$_2$CHNHCO-Tbg-Asp(pyrrolidino)-Asp(cyPn)-γMeLeucinol,

Et$_2$CHNHC(O)-Tbg-Asp(pyrrolidino)-Asp(cyPn)-NHCH$_2$CH$_2$(CH$_3$)$_3$,

Me$_3$CNHC(O)-Tbg-Asp(pyrroidino)-Asp(cyPn)-γMeLeucinol,

Et$_2$CHNHC(O)—NH—(S)—CH(adamantyl)-C(O)-Asp(pyrrolidino)-Asp(cyPn)-γMeLeu-OH,

Et$_2$CHNHC(O)-NH—(S)—CH(adamantyl)-C(O)-Asp(pyrrolidino)-Asp(cyPn)-γMeLeucinol, Et$_2$CHNHC(O)-Tbg-Asp(pyrrolidino)-Asp{(R)-iPr}-Leu-OH, Et$_2$CHNHC(O)-Tbg-Asp(pyrrolidino)-Asp(cyPn)-NHCH$_2$C(CH$_3$)$_3$, Et$_2$CHNHC(O)-Tbg-Asp(pyrrolidino)-Asp{(R)-iPr}-γMeLeucinol, Et$_2$CHNHC(O)-Tbg-Asp(pyrrolidino)-Asp{(R)-iPr}-γMeLeu-OH, Et$_2$CHNHC(O)-Tbg-Asp(pyrrolidino)-Asp(cyPn)-NHCH$_2$CH(CH$_3$)$_2$, Pr$_2$CHNHC(O)-Tbg-Asp(pyrrolidino)-Asp(cyPn)-γMeLeu-OH, Pr$_2$CHNHC(O)-Tbg-Asp(pyrrolidino)-Asp(cyPn)-NHCH$_2$C(CH$_3$)$_3$, (1-propylcyclopentyl)-NHC(O)-Tbg-Asp(pyrrolidino)-Asp(cyPn)-γMeLeu-OEt, Pr$_2$CHNHC(O)-Asp(diMe)- Asp(pyrrolidino)-Asp(cyPn)-γMeLeucinol, Pr$_2$CHNHC(O)-Tbg-Asp(pyrrolidino)-Asp(cyPn)-NHCH(CH$_3$)C(CH$_3$)$_3$, Pr$_2$CHNHC(O)-Tbg-NHCH(3-ethyl-2-oxopentyl)CO-Asp(cyPn)-NHCH$_2$C(CH$_3$)$_3$, Pr$_2$CHNHC(O)-Tbg-NHCH(2-cyclohexyl-2-oxoethyl)C(O)-Asp(cyPn)-NHCH$_2$C(CH$_3$)$_3$, Pr$_2$CHNHC(O)-Tbg-NHCH(2-cyclopentyl-2-oxoethyl)C(O)-Asp(cyPn)-NHCH$_2$C(CH$_3$)$_3$, Pr$_2$CHNHC(O)—N—H—(S)—CH{C(CH$_3$)$_2$OH}C(O)-Asp(pyrrolidino)-Asp(cyPn)-γMeLeucinol, PrMe$_2$CNHC(O)-Tbg-Asp(pyrrolidino)-Asp(cyPn)-γMeLeu-OH, (1-propylcyclopentyl)NHCO-Tbg-Asp(pyrrolidino)-Asp(cyPn)-γMeLeu-OH, Pr$_2$CHNHC(O)-Tbg-NH—(S)—CH(2-cyclobutyl-2-oxoethyl-C(O)-Asp(cyPn)-NHCH$_2$CMe$_3$, Me$_3$CCH$_2$CMe$_2$NHC(O)-Tbg-Asp(pyrrolidino)-Asp(cyPn)-γMeLeu-OH, Pr$_2$CHNHC(O)-Tbg-Asp(pyrrolidino)-Asp(cyPn)-NHCH$_2$-CMe$_2$Et, MePr$_2$CNHC(O)-Tbg-Asp(pyrrolidino)-Asp(cyPn)-NHCH$_2$CMe$_3$, and MePr$_2$CNHC(O)-Tbg-Asp(pyrrolidino)-Asp(cyPn)NH—(R)—CH(Et)CH$_2$CMe$_3$.

* * * * *